United States Patent
Thomas et al.

(10) Patent No.: US 10,745,435 B2
(45) Date of Patent: Aug. 18, 2020

(54) NUCLEIC ACID PRODRUGS

(71) Applicant: CERECOR, INC., Baltimore, MD (US)

(72) Inventors: Stephen B. Thomas, New York, NY (US); Patrick J. Crutcher, New York, NY (US)

(73) Assignee: CERECOR, INC., Rockville, MD (US)

(*) Notice: Subject to any disclaimer, the term of this patent is extended or adjusted under 35 U.S.C. 154(b) by 0 days.

(21) Appl. No.: 15/776,743

(22) PCT Filed: Nov. 16, 2016

(86) PCT No.: PCT/US2016/062271
§ 371 (c)(1),
(2) Date: May 16, 2018

(87) PCT Pub. No.: WO2017/087517
PCT Pub. Date: May 26, 2017

(65) Prior Publication Data
US 2018/0346508 A1   Dec. 6, 2018

Related U.S. Application Data

(60) Provisional application No. 62/255,829, filed on Nov. 16, 2015.

(51) Int. Cl.
| | | |
|---|---|---|
| *C07H 19/20* | (2006.01) | |
| *C07H 19/10* | (2006.01) | |
| *C07H 19/173* | (2006.01) | |
| *C07H 19/073* | (2006.01) | |

(52) U.S. Cl.
CPC ........... *C07H 19/20* (2013.01); *C07H 19/073* (2013.01); *C07H 19/10* (2013.01); *C07H 19/173* (2013.01)

(58) Field of Classification Search
CPC .... C07H 19/073; C07H 19/173; C07H 19/10; C07H 19/20
See application file for complete search history.

(56) References Cited

U.S. PATENT DOCUMENTS

| | | | |
|---|---|---|---|
| 4,172,896 A | 10/1979 | Uno et al. | |
| 5,358,970 A | 10/1994 | Ruff et al. | |
| 5,427,798 A | 6/1995 | Ludwig et al. | |
| 5,541,231 A | 7/1996 | Ruff et al. | |
| 5,731,000 A | 3/1998 | Ruff et al. | |
| 5,763,493 A | 6/1998 | Ruff et al. | |
| 6,110,973 A | 8/2000 | Young | |
| 6,291,498 B1* | 9/2001 | Horn | A61K 9/0048 514/385 |
| 6,420,407 B1* | 7/2002 | Horn | A61K 31/138 514/385 |
| 6,583,124 B2 | 6/2003 | Asgharian | |
| 6,730,065 B1* | 5/2004 | Horn | A61K 31/00 514/385 |
| 6,933,289 B2* | 8/2005 | Lyons | A61K 9/0048 424/488 |

(Continued)

FOREIGN PATENT DOCUMENTS

| | | |
|---|---|---|
| WO | WO-2001/07454 A1 | 2/2001 |
| WO | 2008121634 A2 | 10/2008 |
| WO | WO-2012/117246 A1 | 9/2012 |
| WO | WO-2016/134054 A1 | 8/2016 |

OTHER PUBLICATIONS

Bulst, et al., "In vitro supplementation with deoxynucleoside monophosphates rescues mitochondrial DNA depletion," Mol Genet Metab, 107(0): 95-103 (2012).

(Continued)

*Primary Examiner* — Lawrence E Crane
(74) *Attorney, Agent, or Firm* — Adler Pollock & Sheehan P.C.; Michael Morency

(57) ABSTRACT

The invention relates to deoxynucleotide prodrugs and pharmaceutical preparations thereof. The deoxynucleotide prodrugs include, but are not limited to,

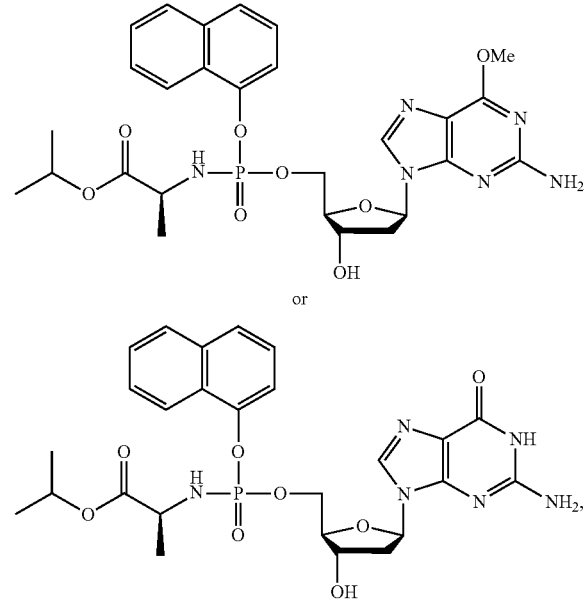

The invention further relates to methods of treatment of a mitochondrial DNA (mtDNA) depletion syndrome (MDS) by administering a therapeutically-effective amount of a deoxynucleotide prodrug of the present invention.

10 Claims, 1 Drawing Sheet

(56) References Cited

U.S. PATENT DOCUMENTS

| | | | | |
|---|---|---|---|---|
| 8,512,717 B2* | 8/2013 | Vehige | ............... | A61K 9/0048 424/400 |
| 8,889,112 B2* | 11/2014 | Horn | ............... | A61K 31/00 424/78.04 |
| 8,992,952 B2* | 3/2015 | Vehige | ............... | A61K 9/0048 424/400 |
| 2005/0004074 A1 | 1/2005 | Lyons et al. | | |
| 2005/0031697 A1 | 2/2005 | Vehige et al. | | |
| 2005/0059744 A1 | 3/2005 | Donello et al. | | |
| 2005/0080056 A1 | 4/2005 | Horn | | |
| 2015/0164863 A1* | 6/2015 | Vehige | ............... | A61K 9/0048 514/413 |

OTHER PUBLICATIONS

International Search Report and Written Opinion for International Application No. PCT/US2016/062271 dated Feb. 27, 2017.
Ora, et al., "Hydrolytic Reactions of Thymidine 5'-O-Phenyl-N-Alkylphosphoramidates, Models of Nucleoside 5'-Monophosphate Prodrugs," Chem Eur J, 13(30): 8591-8599 (2007).
Voorde et al., "The Cytostatic Activity of NUC-3073, a Phosphoramidate Prodrug of 5-fluoro-2'-deoxyuridine, is Independent of Activation by Thymidine Kinase and Insensitive to Degradation by Phosphorolytic Enzymes," Biochem Pharmcol, 82(5): 441-452 (2011).
Buchaklian et al., "Recessive Deoxyguanosine Kinase Deficiency Causes Juvenile onset Mitochondrial Myopathy", Molecular Genetics and Metabolism, vol. 107, Issues 1-2, Sep.-Oct. 2012, pp. 92-94.
Greene et al., "Protective Groups in Organic Synthesis", Third Edition, John Wiley & Sons, Inc., 1999, 52 pages.
Isselbacher et al., "Harrison's Principles of Internal Medicine, 13th Edition", Shock, vol. 5, No. 1, Jan. 1996, 1 page.
Smith, "Compendium of Organic Synthetic Methods", vol. 8, John Wiley & Sons, Inc., 1995, 19 pages.
Venegas et al., "Real-Time Quantitative PCR Analysis of Mitochondrial DNA Content", Current Protocols in Human Genetics, Jan. 15, 2011, Chapter 19.7.1-19.7.12, Supplement 68, 12 pages.
Extended European search report received in European patent Application No. 16867037.0, dated Aug. 16, 2019, 9 Pages.

* cited by examiner

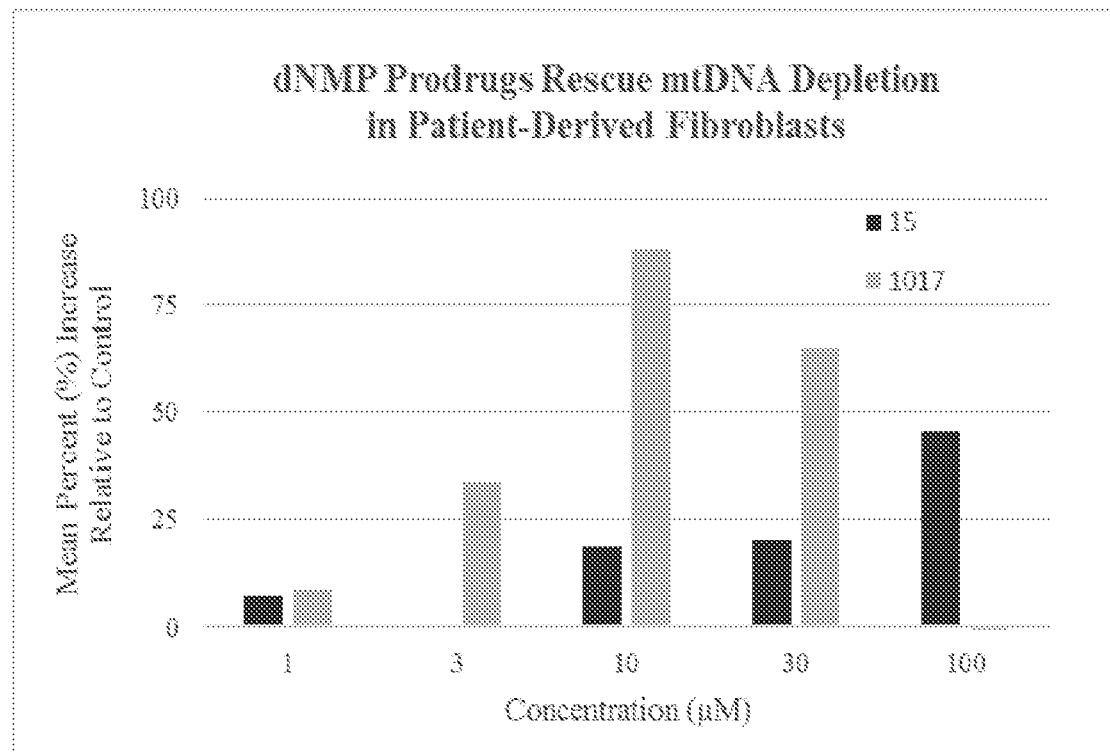

NUCLEIC ACID PRODRUGS

REFERENCE TO RELATED APPLICATIONS

This application is the U.S. National Stage of International Patent Application No. PCT/US2016/062271, filed Nov. 16, 2016 which claims the benefit of U.S. Provisional Patent Application No. 62/255,829, filed Nov. 16, 2015, the contents of each of which are fully incorporated by reference herein.

BACKGROUND OF THE INVENTION

Mitochondrial DNA (mtDNA) depletion syndrome (MDS) encompasses a group of genetic disorders characterized by a severe reduction in mtDNA content leading to respiratory chain deficiency in affected tissues and organs. MDS arises due to defects in mtDNA maintenance caused by mutations in nuclear genes that function in either mitochondrial nucleotide synthesis, deoxyribonucleoside triphosphate (dNTP) metabolism or mtDNA replication. There are also some MDSs with unknown pathophysiology.

Some exemplary MDSs are deoxyguanosine kinase (DGUOK) deficiency, thymidine kinase 2 (TK2) deficiency, mitochondrial neurogastrointestinal encephalomyopathy (MNGIE), mitochondrial DNA polymerase (POLG) deficiencies (including Alpers-Huttenlocher syndrome, SANDO syndrome, MIRAS, etc.), MPV17-related hepatocerebral and RRM2B-related myopathies. Of known mutations, there are over ten genes that have been linked to MDS (TK2, DGUOK, POLG, MPV17, RRM2B, SUCLA2, SUCLG1, TYMP, C10orf2, and SAMHD1).

Direct supplementation with nucleosides, deoxyribonucleoside monophosphates (dNMPs), deoxyribonucleoside diphosphates (dNDPs) or dNTPs has shown the ability to rescue mtDNA depletion in in vitro models of MDS and increase overall survival in animal models of MDS in vivo. However, the pharmacological prospects for nucleosides, dNMPs, dNDPs and dNTPs as practical treatments for MDS in humans are low. The negatively charged phosphates on dNMPs, dNDPs and dNTPs preclude diffusion across cellular membranes. Furthermore, intra- and extracellular phosphatases effectively dephosphorylate dNMPs, dNDPs and dNTPs to the base nucleoside prior to reaching the desired site of action. Although the base nucleoside can enter the cell via passive and active transport mechanisms, it cannot by itself address the deficiencies of MDS given that phosphorylation of a nucleoside to a dNMP is the rate-limiting step of nucleotide synthesis and, in many cases, MDS patients lack the enzyme responsible for this transformation. Such considerations require high doses of nucleosides, dNMPs, dNDPs or dNTPs to potentially achieve therapeutic benefit.

Thus, there is a need for new therapies for MDS, and in particular for therapies that can effectively provide dNMPs, dNDPs or dNTPs to mitochondria.

SUMMARY OF THE INVENTION

In certain embodiments, the present invention provides compounds having the structure of formula (I):

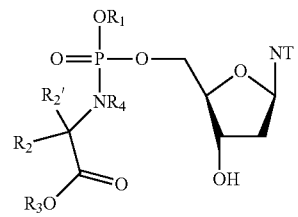

or a pharmaceutically acceptable salt and/or prodrug thereof. In the structure of formula (I):
$R_1$ is aryl or heteroaryl;
$R_2$ and $R_2'$, each independently, are hydrogen, alkyl or aralkyl;
$R_3$ is alkyl or aralkyl;
$R_4$ is hydrogen or alkyl; or
$R_2$ and $R_4$ together with the —C—N— moiety that separates them may form a heterocycle; and
NT is adenine, guanine, cytosine, or thymine, or a nucleobase prodrug moiety such as an adenine, guanine, cytosine, or thymine prodrug moiety.

Exemplary compounds of Formula (I) include the compounds depicted in Table I.

The invention further relates to pharmaceutical compositions of the subject compounds, as well as methods of using these compounds or compositions in the treatment of MDSs such as deoxyguanosine kinase (DGUOK) deficiency, thymidine kinase 2 (TK2) deficiency, mitochondrial neurogastrointestinal encephalomyopathy (MNGIE), mitochondrial DNA polymerase (POLG) deficiencies (including Alpers-Huttenlocher syndrome, SANDO syndrome, MIRAS, etc.), MPV17-related hepatocerebral myopathy, or RRM2B-related myopathy; or in treating a mitochondrial DNA depletion syndrome linked to a mutation in TK2, DGUOK, POLG, MPV17, RRM2B, SUCLA2, SUCLG1, TYMP, C10orf2, or SAMHD1.

BRIEF DESCRIPTION OF THE DRAWINGS

FIG. 1 shows the results of a study on the ability of compounds 15 and 1017 of the present invention to rescue mtDNA depletion in patient-derived fibroblasts.

DETAILED DESCRIPTION OF THE INVENTION

In certain embodiments, the present invention provides compounds having the structure of formula (I):

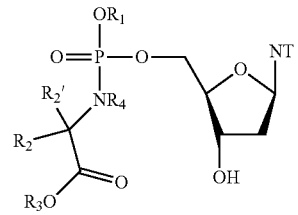

and pharmaceutically acceptable salts and/or prodrugs thereof, wherein: $R_1$ is aryl or heteroaryl; $R_2$ and $R_2'$, each independently, are hydrogen, alkyl or aralkyl; $R_3$ is alkyl or aralkyl; $R_4$ is hydrogen or alkyl; or $R_2$ and $R_4$ together with the —C—N— moiety that separates them may form a heterocycle; and NT is a nucleobase such as adenine, guanine, cytosine, or thymine, or a nucleobase prodrug moiety such as an adenine, guanine, cytosine, or thymine prodrug moiety.

In some embodiments of formula (I), NT is a guanine prodrug moiety with the following structure:

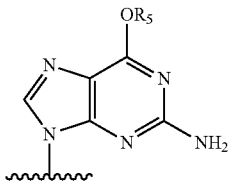

wherein $R_5$ is alkyl or aralkyl. In some embodiments, NT is a thymine prodrug moiety with the following structure:

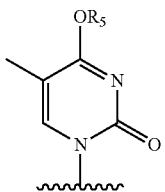

wherein $R_5$ is alkyl or aralkyl. In some preferred embodiments, NT is the moiety with the following structure:

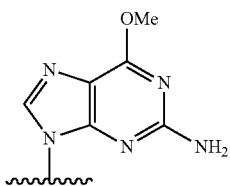 [SMILES: *n1cnc2c(OC)nc(N)nc21]

In some embodiments of formula (I), NT is a nucleobase, such as a natural nucleobase. In some such embodiments, NT is adenine. In other such embodiments, NT is guanine. In still other such embodiments, NT is cytosine. In yet other such embodiments, NT is thymine.

In some embodiments of formula (I), $R_1$ is a $C_6$-$C_{20}$ aryl or a 5-20 atom heteroaryl, such as phenyl, naphthyl, or 4-fluorophenyl. In some preferred embodiments, $R_1$ is naphthyl. In other preferred embodiments, $R_1$ is phenyl.

In some embodiments of formula (I), $R_2$ and $R_2'$, each independently, is selected from hydrogen, $C_1$-$C_6$ alkyl, or $C_7$-$C_{16}$ aralkyl, or a natural amino acid side chain. In some embodiments, $R_2$ is selected from hydrogen or $C_1$-$C_6$ alkyl. In some preferred embodiments, $R_2$ is hydrogen, methyl, isopropyl, or benzyl, most preferably methyl. In other preferred embodiments, $R_2$ is a natural amino acid side chain. In some preferred embodiments, $R_2'$ is methyl. In other preferred embodiments, $R_2'$ is H.

In some embodiments of formula (I), the carbon to which $R_2$ is attached is in the S-configuration. In other embodiments, the carbon to which $R_2$ is attached is in the R-configuration. In some embodiments, the carbon to which $R_2$ is attached is in the D-configuration. In certain preferred embodiments, the carbon to which $R_2$ is attached is in the L-configuration (i.e., $R_2$ is disposed in the L-configuration). According to these embodiments, the remainder of the variables in formula (I) may be selected as described above and below.

In some embodiments of formula (I), $R_3$ is selected from $C_1$-$C_6$ alkyl or $C_7$-$C_{16}$ aralkyl, such as $C_1$-$C_6$ alkyl or $C_7$-$C_{11}$ aralkyl. In some preferred embodiments, $R_3$ is hydrogen, methyl, isopropyl, neopentyl, or benzyl.

In some embodiments of formula (I), $R_4$ is selected from hydrogen or $C_1$-$C_6$ alkyl, such as hydrogen or $C_1$-$C_3$ alkyl, e.g., methyl, ethyl, propyl, or isopropyl. In some preferred embodiments, $R_4$ is methyl. In other preferred embodiments, $R_4$ is hydrogen.

In some embodiments, $R_2$ and $R_4$, together with the —C—N— moiety that separates them, form a 5-10-atom heterocycle, such as a 5-atom heterocycle. In some preferred embodiments, $R_2$ and $R_4$, together with the —C—N— moiety that separates them, form a pyrrolidine ring, e.g., as in proline.

In some embodiments of formula (I), $R_5$ is selected from $C_1$-$C_6$ alkyl or $C_7$-$C_{16}$ aralkyl, such as $C_1$-$C_6$ alkyl or $C_7$-$C_{11}$ aralkyl e.g., methyl, ethyl, isopropyl, or benzyl. In some preferred embodiments, $R_5$ is ethyl. In some preferred embodiments, $R_5$ is methyl.

In certain embodiments, the present invention provides compounds having the structure of formula (Ia):

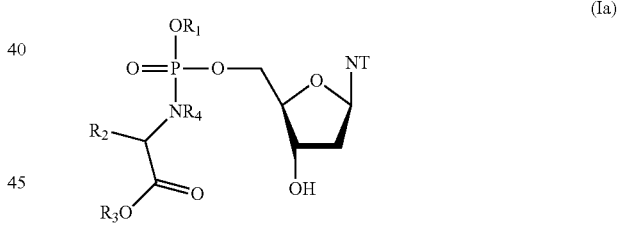

and pharmaceutically acceptable salts and/or prodrugs thereof, wherein: $R_1$ is aryl or heteroaryl; $R_2$ is hydrogen, alkyl or aralkyl; $R_3$ is alkyl or aralkyl; $R_4$ is hydrogen or alkyl; and NT is adenine, guanine, cytosine, or thymine.

In further embodiments of formula (Ia), $R_1$ is phenyl, naphthyl, or 4-fluorophenyl; $R_2$ is methyl and the carbon to which $R_2$ is attached is in the L-configuration; $R_3$ is methyl, benzyl, or isopropyl; or $R_4$ is hydrogen. In further embodiments, $R_1$ is phenyl, naphthyl, or 4-fluorophenyl; $R_2$ is methyl and the carbon to which $R_2$ is attached is in the L-configuration; $R_3$ is methyl, benzyl, or isopropyl; and $R_4$ is hydrogen. In some preferred embodiments, $R_1$ is naphthyl. In some preferred embodiments, $R_1$ is phenyl.

In certain embodiments, the invention relates to compounds of the structures depicted in Table 1 and pharmaceutically acceptable salts and prodrugs thereof.

TABLE 1
A
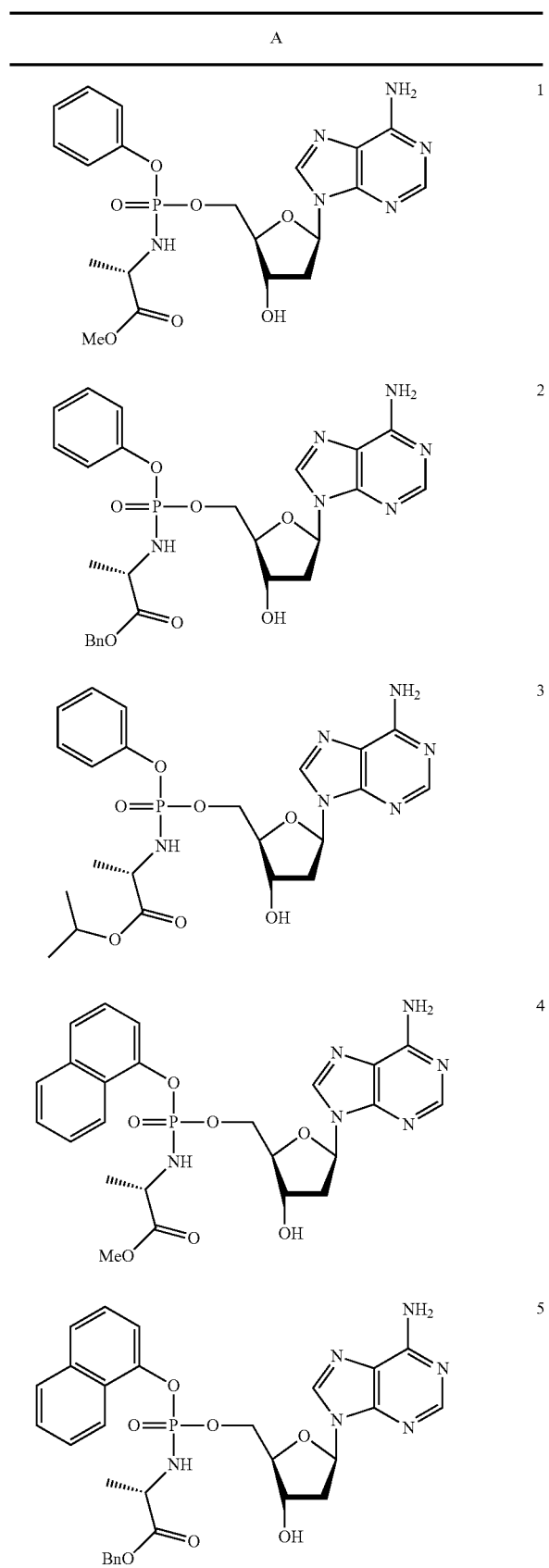
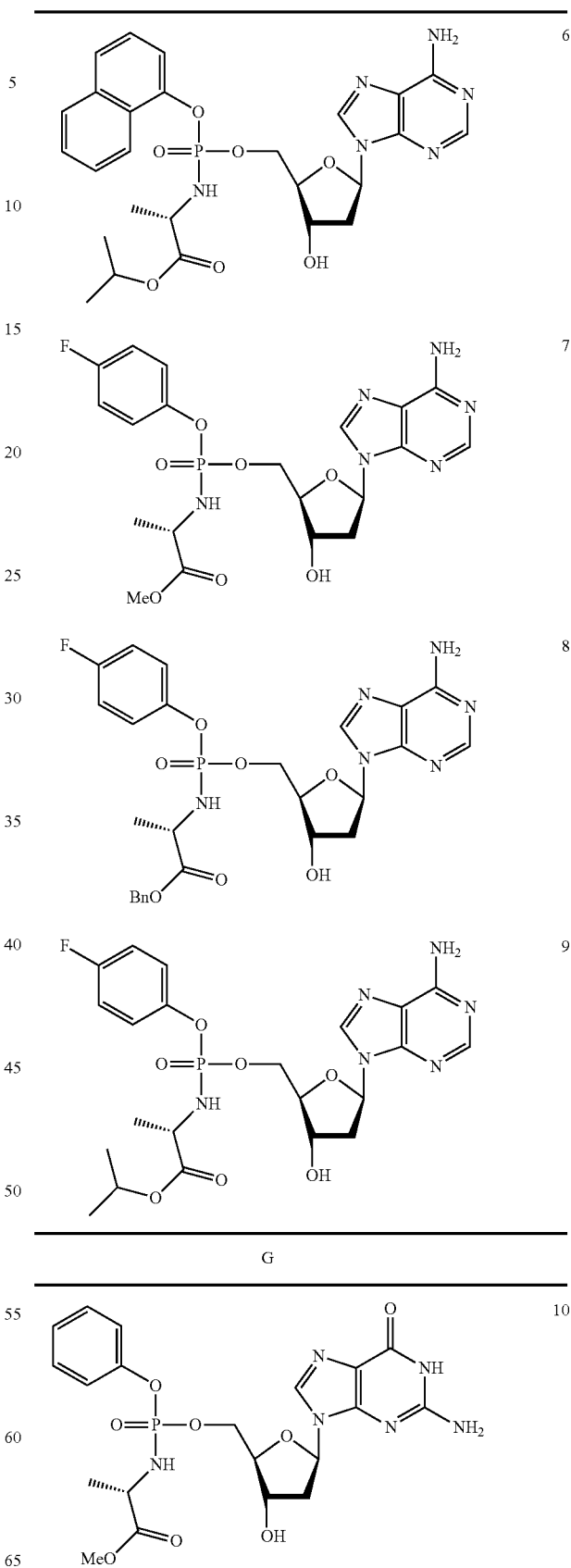

TABLE 1-continued
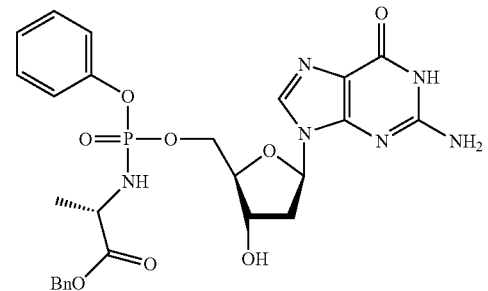 [SMILES: C[C@H](NP(=O)(OC[C@H]1O[C@@H](n2cnc3c(=O)[nH]c(N)nc32)C[C@H]1O)Oc1ccccc1)C(=O)OCc1ccccc1] 11
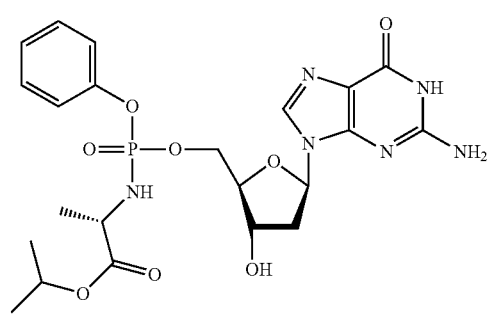 [SMILES: CC(C)OC(=O)[C@H](C)NP(=O)(OC[C@H]1O[C@@H](n2cnc3c(=O)[nH]c(N)nc32)C[C@H]1O)Oc1ccccc1] 12
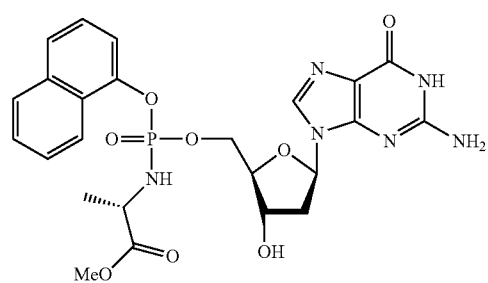 13
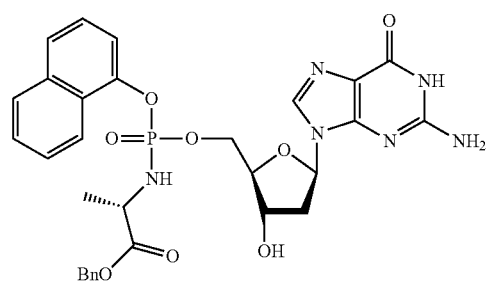 [SMILES: COC(=O)[C@H](C)NP(=O)(OC[C@H]1O[C@@H](n2cnc3c(=O)[nH]c(N)nc32)C[C@H]1O)Oc1cccc2ccccc12] 14
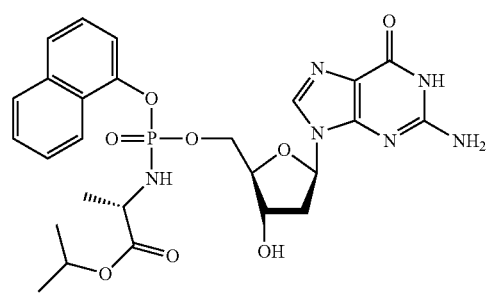 [SMILES: CC(C)OC(=O)[C@H](C)NP(=O)(OC[C@H]1O[C@@H](n2cnc3c(=O)[nH]c(N)nc32)C[C@H]1O)Oc1cccc2ccccc12] 15
TABLE 1-continued
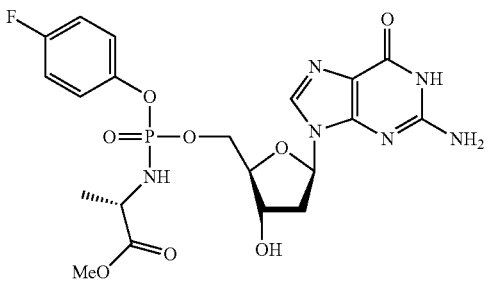 [SMILES: COC(=O)[C@H](C)NP(=O)(OC[C@H]1O[C@@H](n2cnc3c(=O)[nH]c(N)nc32)C[C@H]1O)Oc1ccc(F)cc1] 16
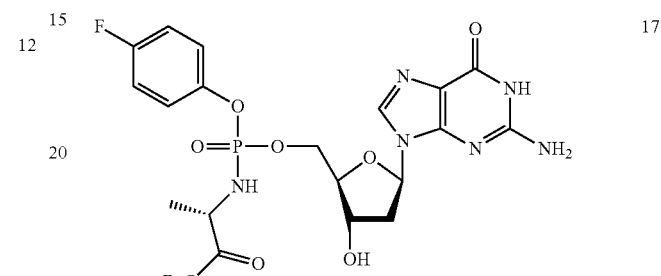 17
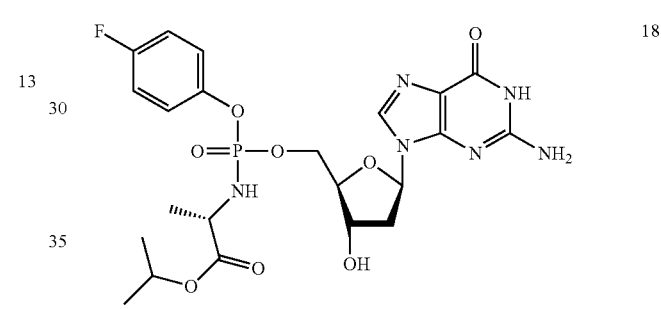 18
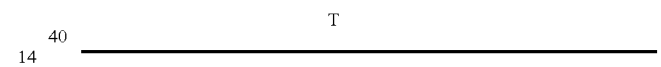
T
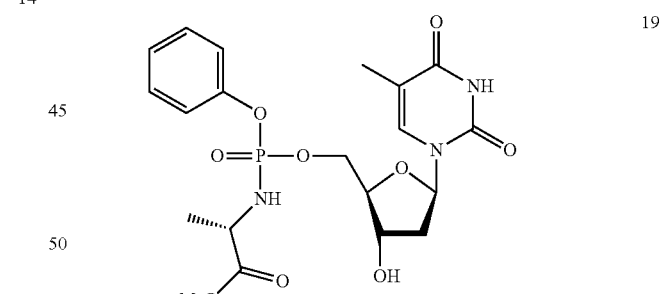 19
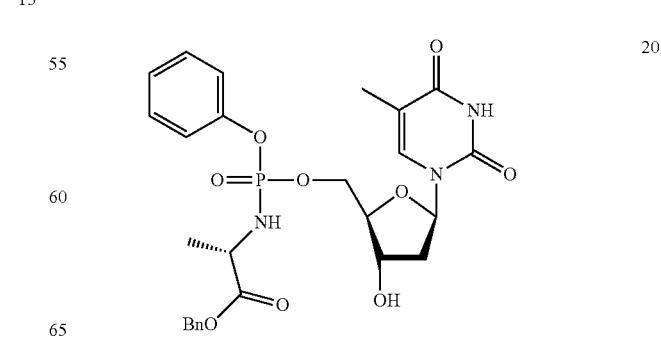 20

TABLE 1-continued
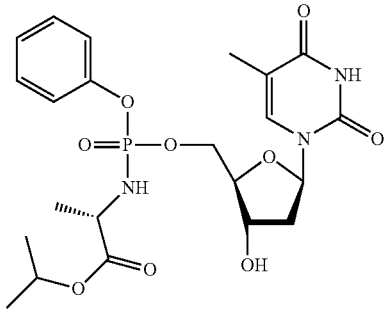 [SMILES: Cc1cn([C@H]2C[C@@H](O)[C@@H](COP(=O)(N[C@@H](C)C(=O)OC(C)C)Oc3ccccc3)O2)c(=O)[nH]c1=O] 21
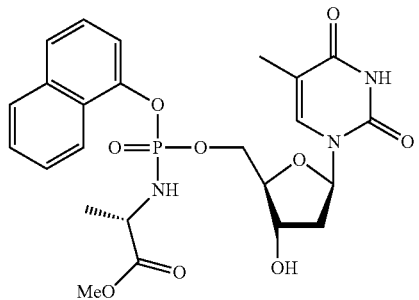 22
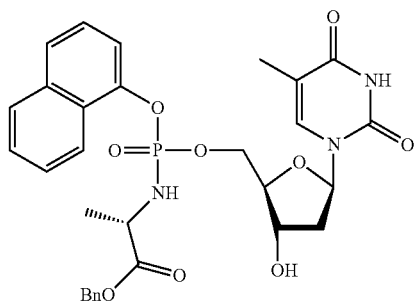 [SMILES: Cc1cn([C@H]2C[C@@H](O)[C@@H](COP(=O)(N[C@@H](C)C(=O)OCc3ccccc3)Oc3cccc4ccccc34)O2)c(=O)[nH]c1=O] 23
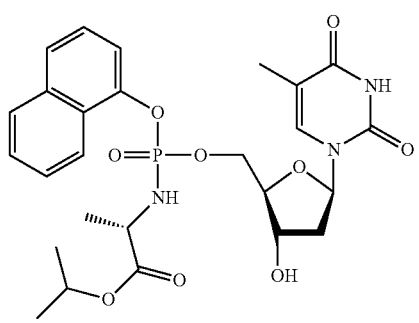 [SMILES: Cc1cn([C@H]2C[C@@H](O)[C@@H](COP(=O)(N[C@@H](C)C(=O)OC(C)C)Oc3cccc4ccccc34)O2)c(=O)[nH]c1=O] 24
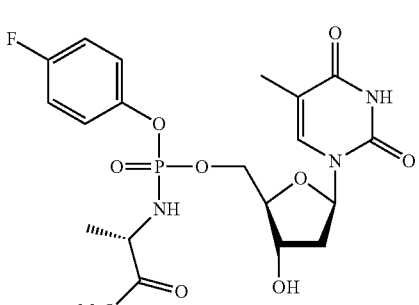 25
TABLE 1-continued
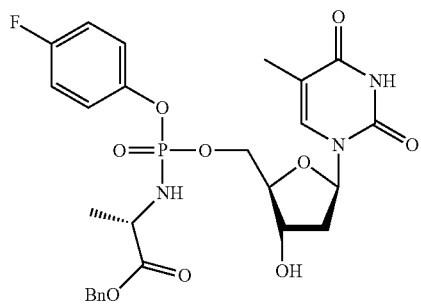 [SMILES: Cc1cn([C@H]2C[C@@H](O)[C@@H](COP(=O)(N[C@@H](C)C(=O)OCc3ccccc3)Oc3ccc(F)cc3)O2)c(=O)[nH]c1=O] 26
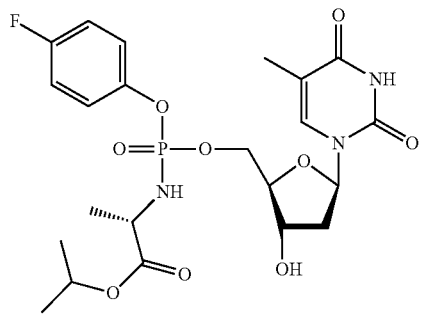 [SMILES: Cc1cn([C@H]2C[C@@H](O)[C@@H](COP(=O)(N[C@@H](C)C(=O)OC(C)C)Oc3ccc(F)cc3)O2)c(=O)[nH]c1=O] 27
C
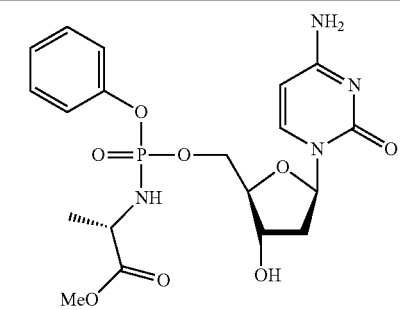 28
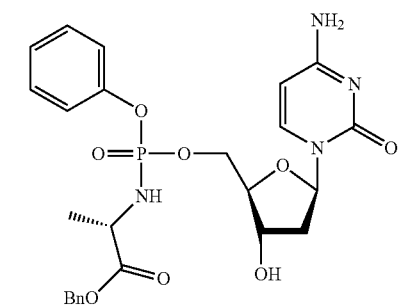 [SMILES: COC(=O)[C@H](C)NP(=O)(OC[C@H]1O[C@@H](n2ccc(N)nc2=O)C[C@H]1O)Oc1ccccc1] 29
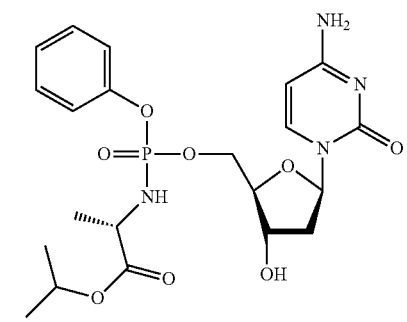 [SMILES: CC(C)OC(=O)[C@H](C)NP(=O)(OC[C@H]1O[C@@H](n2ccc(N)nc2=O)C[C@H]1O)Oc1ccccc1] 30

TABLE 1-continued

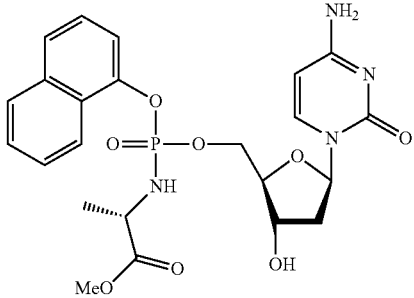 [SMILES: COC(=O)[C@H](C)NP(=O)(OC[C@H]1O[C@@H](n2ccc(N)nc2=O)C[C@H]1O)Oc1cccc2ccccc12] 31

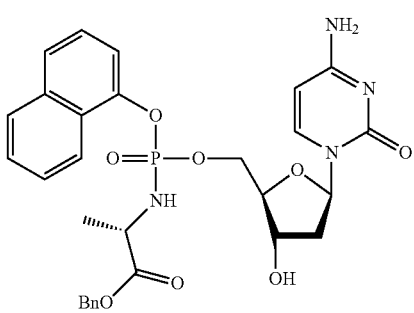 [SMILES: C[C@H](NP(=O)(OC[C@H]1O[C@@H](n2ccc(N)nc2=O)C[C@H]1O)Oc1cccc2ccccc12)C(=O)OCc1ccccc1] 32

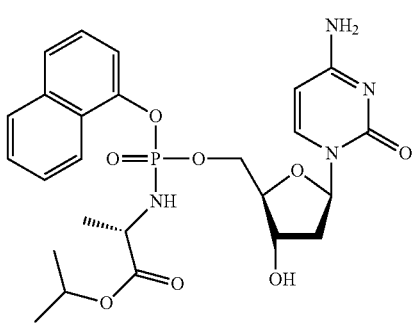 [SMILES: CC(C)OC(=O)[C@H](C)NP(=O)(OC[C@H]1O[C@@H](n2ccc(N)nc2=O)C[C@H]1O)Oc1cccc2ccccc12] 33

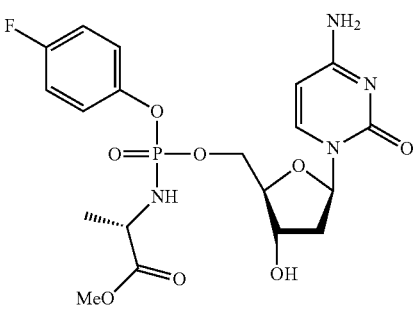 34

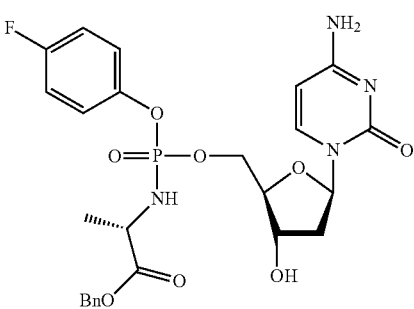 [SMILES: C[C@H](NP(=O)(OC[C@H]1O[C@@H](n2ccc(N)nc2=O)C[C@H]1O)Oc1ccc(F)cc1)C(=O)OCc1ccccc1] 35

TABLE 1-continued

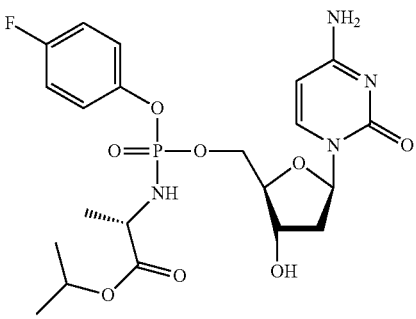 [SMILES: CC(C)OC(=O)[C@H](C)NP(=O)(OC[C@H]1O[C@@H](n2ccc(N)nc2=O)C[C@H]1O)Oc1ccc(F)cc1] 36

In some preferred embodiments of formula (I), the compound is Compound 1017:

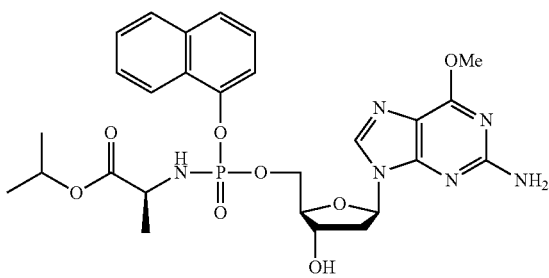

or a pharmaceutically acceptable salt thereof.

In some preferred embodiments of formula (I) or formula (Ia), the compound is Compound 15:

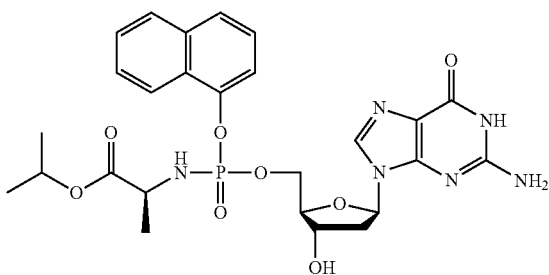

These compounds are prodrugs of dNMPs, and can be used to treat MDSs, or for any other purpose for which dNMP prodrugs, or dNMPs themselves, are useful in the treatment of disease.

These compounds are expected to have desirable physicochemical properties, given their calculated log P (octanol-water partition), log S (solubility in water), and TPSA (total polar surface area) values all indicate that they will efficiently cross cell membranes and be readily solvated in biological fluids. Those calculated values are given in Table 2.

TABLE 2

| Compound | NT | $R_1$ | $R_2$ | $R_3$ | $R_4$ | log P | log S | TPSA |
|---|---|---|---|---|---|---|---|---|
| 1 | A | Ph | L-Me | Me | H | 0.34 | −3.73 | 173 |
| 2 | A | Ph | L-Me | Bn | H | 2.12 | −5.49 | 173 |
| 3 | A | Ph | L-Me | iPr | H | 1.14 | −4.38 | 173 |
| 4 | A | Np | L-Me | Me | H | 1.56 | −5.60 | 173 |

TABLE 2-continued

| Compound | NT | R₁ | R₂ | R₃ | R₄ | log P | log S | TPSA |
|---|---|---|---|---|---|---|---|---|
| 5 | A | Np | L-Me | Bn | H | 3.34 | −7.37 | 173 |
| 6 | A | Np | L-Me | iPr | H | 2.36 | −6.26 | 173 |
| 7 | A | 4-FPh | L-Me | Me | H | 0.49 | −4.02 | 173 |
| 8 | A | 4-FPh | L-Me | Bn | H | 2.28 | −5.79 | 173 |
| 9 | A | 4-FPh | L-Me | iPr | H | 1.29 | −4.67 | 173 |
| 10 | G | Ph | L-Me | Me | H | −0.23 | −3.43 | 189 |
| 11 | G | Ph | L-Me | Bn | H | 1.55 | −5.20 | 189 |
| 12 | G | Ph | L-Me | iPr | H | 0.57 | −4.08 | 189 |
| 13 | G | Np | L-Me | Me | H | 0.99 | −5.31 | 189 |
| 14 | G | Np | L-Me | Bn | H | 2.77 | −7.07 | 189 |
| 15 | G | Np | L-Me | iPr | H | 1.79 | −5.96 | 189 |
| 16 | G | 4-FPh | L-Me | Me | H | −0.08 | −3.72 | 189 |
| 17 | G | 4-FPh | L-Me | Bn | H | 1.71 | −5.49 | 189 |
| 18 | G | 4-FPh | L-Me | iPr | H | 0.72 | −4.38 | 189 |
| 19 | T | Ph | L-Me | Me | H | −0.15 | −2.65 | 153 |
| 20 | T | Ph | L-Me | Bn | H | 1.64 | −4.42 | 153 |
| 21 | T | Ph | L-Me | iPr | H | 0.65 | −3.31 | 153 |
| 22 | T | Np | L-Me | Me | H | 1.07 | −4.53 | 153 |
| 23 | T | Np | L-Me | Bn | H | 2.86 | −6.30 | 153 |
| 24 | T | Np | L-Me | iPr | H | 1.87 | −5.18 | 153 |
| 25 | T | 4-FPh | L-Me | Me | H | 0.00 | −2.95 | 153 |
| 26 | T | 4-FPh | L-Me | Bn | H | 1.79 | −4.71 | 153 |
| 27 | T | 4-FPh | L-Me | iPr | H | 0.81 | −3.60 | 153 |
| 28 | C | Ph | L-Me | Me | H | 0.13 | −2.83 | 162 |
| 29 | C | Ph | L-Me | Bn | H | 1.91 | −4.60 | 162 |
| 30 | C | Ph | L-Me | iPr | H | 0.93 | −3.49 | 162 |
| 31 | C | Np | L-Me | Me | H | 1.35 | −4.71 | 162 |
| 32 | C | Np | L-Me | Bn | H | 3.13 | −6.48 | 162 |
| 33 | C | Np | L-Me | iPr | H | 2.15 | −5.37 | 162 |
| 34 | C | 4-FPh | L-Me | Me | H | 0.28 | −3.13 | 162 |
| 35 | C | 4-FPh | L-Me | Bn | H | 2.07 | −4.90 | 162 |
| 36 | C | 4-FPh | L-Me | iPr | H | 1.08 | −3.78 | 162 |

In certain embodiments, compounds of the invention may be prodrugs of the compounds of Table I, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomers. For example, a compound of the invention may have greater than 30% de, 40% de, 50% de, 60% de, 70% de, 80% de, 90% de, or even 95% or greater de.

In certain embodiments, the present invention relates to methods of treatment with a compound of formula (I) or (Ia), or a compound selected from Table I, or a pharmaceutically acceptable salt thereof. In certain embodiments, the method comprises administering the compound to a patient in need thereof. In certain embodiments, the therapeutic preparation may be enriched to provide predominantly one enantiomer of a compound (e.g., of a compound selected from Table I). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of a compound selected from Table 1). A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound selected from Table I, or a pharmaceutically acceptable salt thereof. In certain embodiments, the therapeutic preparation may be enriched to provide predominantly one enantiomer of a compound (e.g., of a compound selected from Table 1). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of a compound selected from Table 1). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention, such as a compound of Formula (I) or (Ia) or a compound selected from Table 1), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —$CN$ and the like. Exemplary substituted alkyls are described below. Cycloalkyls can be further substituted with alkyls, alkenyls, alkoxys, alkylthios, aminoalkyls, carbonyl-substituted alkyls, —$CF_3$, —$CN$, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

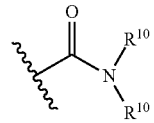

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

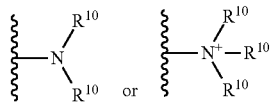

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

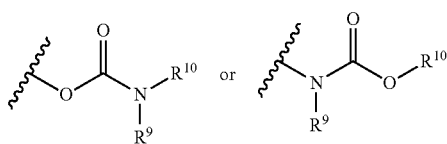

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "natural amino acid" refers to one of the twenty natural amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. As used herein, the term "natural amino acid" encompasses all stereoisomers, such as the D- and the L-stereoisomers. The term "natural amino acid side chain" refers to one of the side chains on the twenty natural amino acids, that is, the substituent on the α-carbon or, in the case of proline, the propylene moiety linking the α-carbon with the amino group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

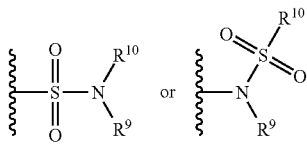

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

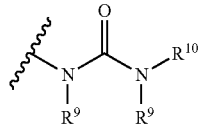

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. For example, a compound that prevents epilepsy may reduce the frequency of seizures and/or reduce the severity of seizures.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention (e.g., a compound selected from Table I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds selected from Table I in a formulation represented above can be replaced with the corresponding suitable prodrug, e.g., wherein a hydroxyl in the parent compound is presented as an ester or a carbonate or carboxylic acid present in the parent compound is presented as an ester.

Use of Deoxynucleotide Prodrugs

In some embodiments, the present invention provides a method of treating a patient suffering from MDS, comprising administering to the patient a therapeutically effective amount of a compound of Formula (I) or (Ia). In some embodiments, the MDS is selected from DGUOK deficiency, TK2 deficiency, MNGIE, POLG deficiency, Alpers-Huttenlocher syndrome, SANDO syndrome, MIRAS, MPV17-related hepatocerebral myopathy, or RRM2B-related myopathy. In some embodiments, the MDS is an RRM2B-related myopathy. In some embodiments, the MDS is linked to a mutation in TK2, DGUOK, POLG, MPV17, RRM2B, SUCLA2, SUCLG1, TYMP, C10orf2, or SAMHD1. In some embodiments, the MDS has unknown pathophysiology.

In some embodiments, the dAMP and dGMP prodrugs of the present invention, i.e., the compounds of Formula (I) or (Ia) wherein NT is adenine or guanine, may be used to treat DGUOK deficiency.

In some embodiments, the dAMP and dGMP prodrugs of the present invention, i.e., the compounds of Formula (I) or (Ia) wherein NT is adenine or guanine or an adenine or guanine prodrug moiety, may be used to treat DGUOK deficiency.

In other embodiments, the dCTP and dTTP prodrugs of the present invention, i.e., the compounds of Formula (I) or (Ia) wherein NT is cytosine or thymine, may be used to treat TK2 deficiency.

In other embodiments, the dCTP and dTTP prodrugs of the present invention, i.e., the compounds of Formula (I) or (Ia) wherein NT is cytosine or thymine or a cytosine or thymine prodrug moiety, may be used to treat TK2 deficiency.

In certain embodiments, the dCTP prodrugs of the present invention, i.e., the compounds of Formula (I) or (Ia) wherein NT is cytosine, may be used to treat MNGIE.

In certain embodiments, the dCTP prodrugs of the present invention, i.e., the compounds of Formula (I) or (Ia) wherein NT is cytosine or a cytosine prodrug moiety, may be used to treat MNGIE.

In some embodiments, the dAMP, dGMP, dCTP, and dTTP prodrugs of the present invention, i.e., the compounds of Formula (I) or (Ia) wherein NT is adenine, guanine, cytosine, or thymine, may be used to treat POLG deficiency. In certain such embodiments, NT is adenine or guanine.

In some embodiments, the dAMP, dGMP, dCTP, and dTTP prodrugs of the present invention, i.e., the compounds of Formula (I) or (Ia) wherein NT is adenine, guanine, cytosine, or thymine or an adenine, guanine, cytosine, or thymine prodrug moiety, may be used to treat POLG deficiency. In certain such embodiments, NT is adenine or guanine or an adenine or guanine prodrug moiety.

In some embodiments, the dAMP and dGMP prodrugs of the present invention, i.e., the compounds of Formula (I) or (Ia) wherein NT is adenine or guanine or an adenine or guanine prodrug moiety, may be used to treat MPV17. In certain such embodiments, NT is adenine or guanine.

In some embodiments, the dAMP, dGMP, dCTP, and dTTP prodrugs of the present invention, i.e., the compounds of Formula (I) or (Ia) wherein NT is adenine, guanine, cytosine, or thymine or an adenine, guanine, cytosine, or thymine prodrug moiety, may be used to treat a mitochondrial DNA depletion syndrome that is linked to a mutation in SAMDH1. In certain such embodiments, NT is adenine, guanine, thymine or cytosine.

In some embodiments, the dAMP, dGMP, dCTP, and dTTP prodrugs of the present invention, i.e., the compounds of Formula (I) or (Ia) wherein NT is adenine, guanine, cytosine, or thymine or an adenine, guanine, cytosine, or thymine prodrug moiety, may be used to treat a mitochondrial DNA depletion syndrome that is linked to a mutation in RR2MB. In certain such embodiments, NT is adenine, guanine, thymine or cytosine.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

Exemplification

The invention now being generally described, it will be more readily understood by reference to the following examples, which are included merely for purposes of illustration of certain aspects and embodiments of the present invention, and are not intended to limit the invention.

EXAMPLES

Example 1

Synthetic Protocols (Method A)

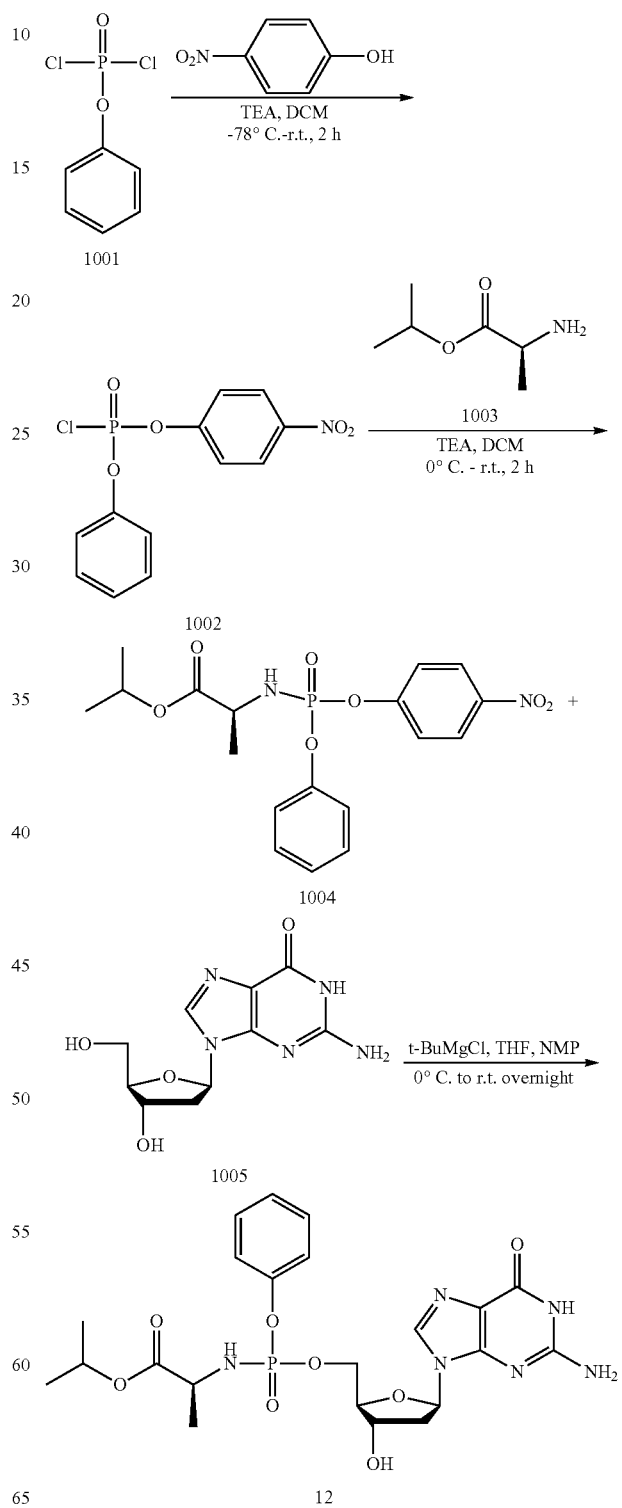

General Procedure for the Preparation of Compound 12 isopropyl ((((2R,3S,5R)-5-(2-amino-6-oxo-1,6-dihydro-9H-purin-9-yl)-3-hydroxytetrahydrofuran-2-yl)methoxy)(phenoxy)phosphoryl)-L-alaninate To a solution of compound 1001 (25.0 g, 118.5 mmol, 1.0 eq) in dichloromethane (250 mL) at −78° C. was added a solution of 4-nitrophenol (16.5 g, 118.5 mmol, 1.0 eq) in dichloromethane (250 mL) and TEA (18 mL, 130.3 mmol, 1.1 eq). The reaction mixture was warmed to room temperature, stirred for 1 h, and cooled to 0° C. A solution of compound 1003 (19.9 g, 118.5 mmol, 1.0 eq) and triethylamine (34.5 mL, 248.9 mmol, 2.1 eq) in dichloromethane (250 mL) was added. The mixture was warmed to room temperature, stirred for 2 h, and quenched with water (500 mL). The organic layer was separated, dried over sodium sulfate, filtered, and concentrated under reduced pressure. The crude product was purified by flash column chromatography on silica gel ($Et_2O$/EtOAc=2/1) to give compound 1004 (25.0 g, 52%) as colorless oil. LC-MS: 409.2 [M+H]$^+$, expected 409.11, $^1$H NMR (400 MHz, $CDCl_3$) (δ, ppm) 8.18 (d, J=8.7 Hz, 2H), 7.34 (ddd, J=15.9, 12.9, 5.1 Hz, 4H), 7.27-7.08 (m, 3H), 4.98 (m, 1H), 4.36-4.16 (m, 1H), 1.35 (d, J=7.0 Hz, 3H), 1.24-1.15 (m, 6H).

To a solution of compound 1005 (2.6 g, 9.8 mmol, 1.0 eq) in THF (7.5 mL) and NMP (30 mL) at 0° C. was added 1.0 M t-BuMgCl (14.8 mL, 14.7 mmol, 1.5 eq). The mixture was stirred at 0° C. for 0.5 h and a solution of compound 1004 (3.0 g, 7.35 mmol, 0.75 eq) in THF (10 mL) was added. The mixture was warmed to room temperature and stirred overnight. A saturated aqueous solution of $NH_4Cl$ (30 mL) was added and the organic phase was extracted with ethyl acetate (2+50 mL). The combined organic layer was dried with sodium sulfate, filtered, and concentrated. The crude product was purified by column chromatography on silica gel twice (DCM–DCM/MeOH=15/1) to afford compound 12 (600 mg, 17%, >95% purity) as a white solid.

The Following Compounds were Prepared According to the General Procedure Described in Method A via Displacement of the 4-nitrophenol Leaving Group with the Appropriate deoxynucleoside Base.

| Comp. No. | IUPAC Name | Observed MW (Expected) | $^1$H NMR (400 MHz) |
|---|---|---|---|
| 12 (G) | isopropyl ((((2R,3S,5R)-5-(2-amino-6-oxo-1,6-dihydro-9H-purin-9-yl)-3-hydroxytetrahydrofuran-2-yl)methoxy)(phenoxy)phosphoryl)-L-alaninate | 537.2 (537.3) | $CD_3OD$ (δ, ppm) 7.97 (s, 1H), 7.35-7.25 (m, 2H), 7.17 (td, J = 15.9, 7.5 Hz, 3H), 6.28 (dd, J = 13.6, 6.5 Hz, 1H), 4.59 (m, 1H), 4.37 (m, 2H), 4.28 (m, 1H), 4.16 (m, 1H), 3.86 (m, 1H), 2.66 (m, 1H), 2.40 (m, 1H), 1.28 (t, J = 6.4 Hz, 3H), 1.23-1.14 (m, 6H) |
| 18 (G) | isopropyl ((((2R,3S,5R)-5-(2-amino-6-oxo-1,6-dihydro-9H-purin-9-yl)-3-hydroxytetrahydrofuran-2-yl)methoxy)(4-fluorophenoxy)phosphoryl)-L-alaninate | 555.2 (555.2) | $CD_3OD$ (δ, ppm) 7.92 (m, 1H), 7.30-7.15 (m, 2H), 7.05 (m, 2H), 6.28 (m, 1H), 4.59 (m, 1H), 4.37 (m, 2H), 4.28 (m, 1H), 4.16 (m, 1H), 3.84 (m, 1H), 2.70 (m, 1H), 2.38 (m, 1H), 1.24 (t, J = 6.4 Hz, 3H), 1.23-1.14 (m, 6H) |
| 15 (G) | isopropyl ((((2R,3S,5R)-5-(2-amino-6-oxo-1,6-dihydro-9H-purin-9-yl)-3-hydroxytetrahydrofuran-2-yl)methoxy)(naphthalen-1-yloxy)phosphoryl)-L-alaninate | 587.2 (587.3) | $CD_3OD$ (δ, ppm) 8.10 (m, 1H), 7.88 (m, 1H), 7.68 (m, 1H), 7.50 (m, 3H), 7.38 (m, 2H), 6.24 (m, 1H), 4.55 (m, 1H), 4.40 (m, 2H), 4.36 (m, 1H), 4.18 (m, 1H), 3.98 (m, 1H), 2.45 (m, 1H), 2.30 (m, 1H), 1.28 (m, 3H), 1.20-1.14 (m, 6H) |
| 21 (T) | isopropyl ((((2R,3S,5R)-3-hydroxy-5-(5-methyl-2,4-dioxo-3,4-dihydropyrimidin-1(2H)-yl)tetrahydrofuran-2-yl)methoxy)(phenoxy)phosphoryl)-L-alaninate | 512.2 (512.3) | $CDCl_3$ (δ, ppm) 8.85 (brs, 1H), 7.39-7.28 (m, 3H), 7.24-7.11 (m, 3H), 6.25 (m, 1H), 5.08-4.90 (m, 1H), 4.48 (m, 1H), 4.32 (m, 1H), 4.10-3.90 (m, 3H), 3.80-3.60 (m, 1H), 2.42-2.29 (m, 1H), 2.12 (m, 1H), 1.89 (d, J = 3.6 Hz, 3H), 1.77 (m, 1H), 1.35 (m, 3H), 1.22 (m, 6H) |
| 27 (T) | isopropyl ((4-fluorophenoxy)(((2R,3S,5R)-3-hydroxy-5-(5-methyl-2,4-dioxo-3,4-dihydropyrimidin-1(2H)-yl)tetrahydrofuran-2-yl)methoxy)phosphoryl)-L-alaninate | 530.2 (530.3) | $CDCl_3$ (δ, ppm) 9.49 (s, 1H), 7.35 (s, 1H), 7.16 (m, 2H), 6.99 (m, 2H), 6.27 (m, 1H), 5.05-4.84 (m, 1H), 4.47 (m, 1H), 4.31 (m, 2H), 4.21 (m, 1H), 4.08 (m, 1H), 4.00-3.87 (m, 1H), 2.36 (s, 1H), 2.15 (m, 2H), 1.85 (d, J = 19.8 Hz, 3H), 1.34 (t, J = 7.6 Hz, 3H), 1.20 (m, 6H) |
| 24 (T) | isopropyl ((((2R,3S,5R)-3-hydroxy-5-(5-methyl-2,4-dioxo-3,4-dihydropyrimidin-1(2H)-yl)tetrahydrofuran-2- | 562.2 (562.2) | $CDCl_3$ (δ, ppm) 8.85 (m, 1H), 8.05 (m, 1H), 7.83 (m, 1H), 7.65 (m, 1H), 7.57-7.44 (m, 3H), 7.44-7.33 (m, 2H), |

-continued

| Comp. No. | IUPAC Name | Observed MW (Expected) | $^1$H NMR (400 MHz) |
|---|---|---|---|
| | yl)methoxy)(naphthalen-1-yloxy)phosphoryl)-L-alaninate | | 7.31 (m, 1H), 6.24 (m, 1H), 5.01-4.87 (m, 1H), 4.39 (m, 3H), 4.05 (m, 4H), 2.28 (m, 1H), 1.98 (m, 1H), 1.78 (d, J = 18.6 Hz, 3H), 1.32 (dd, J = 10.9, 6.8 Hz, 3H), 1.20 (d, J = 6.2 Hz, 3H), 1.16 (dd, J = 9.4, 6.3 Hz, 3H) |
| 30 (C) | isopropyl ((((2R,3S,5R)-5-(4-amino-2-oxopyrimidin-1(2H)-yl)-3-hydroxytetrahydrofuran-2-yl)methoxy)(phenoxy)phosphoryl)-L-alaninate | 497.2 (497.5) | CD$_3$OD (δ, ppm) 7.82 (m, 1H), 7.38 (m, 2H), 7.22 (m, 3H), 6.24 (m, 1H), 5.84 (m, 1H), 4.38 (m, 2H), 4.30 (m, 2H), 4.14 (m, 1H), 3.90 (m, 1H), 2.32 (m, 1H), 1.98 (m, 1H), 1.34 (m, 3H), 1.20 (m, 6H) |
| 36 (C) | isopropyl ((((2R,3S,5R)-5-(4-amino-2-oxopyrimidin-1(2H)-yl)-3-hydroxytetrahydrofuran-2-yl)methoxy)(4-fluorophenoxy)phosphoryl)-L-alaninate | 515.2 (515.4) | CD$_3$OD (δ, ppm) 7.82 (m, 1H), 7.28 (m, 2H), 7.08 (m, 3H), 6.28 (m, 1H), 5.94 (m, 1H), 4.38 (m, 2H), 4.30 (m, 2H), 4.10 (m, 1H), 3.90 (m, 1H), 2.36 (m, 1H), 2.04 (m, 1H), 1.34 (m, 3H), 1.24 (m, 6H) |
| 33 (C) | isopropyl ((((2R,3S,5R)-5-(4-amino-2-oxopyrimidin-1(2H)-yl)-3-hydroxytetrahydrofuran-2-yl)methoxy)(naphthalen-1-yloxy)phosphoryl)-L-alaninate | 547.2 (547.3) | CD$_3$OD (δ, ppm) 8.18 (m, 1H), 7.88 (m, 1H), 7.70 (m, 1H), 7.56 (m, 3H), 7.54 (m, 1H), 7.44 (m, 1H), 6.20 (m, 1H), 5.76 (m, 1H), 4.38 (m, 1H), 4.30 (m, 3H), 4.10 (m, 1H), 3.98 (m, 1H), 2.18 (m, 1H), 1.64 (m, 1H), 1.34 (m, 3H), 1.22 (m, 6H) |

Example 1

Synthetic Protocols (Method B)

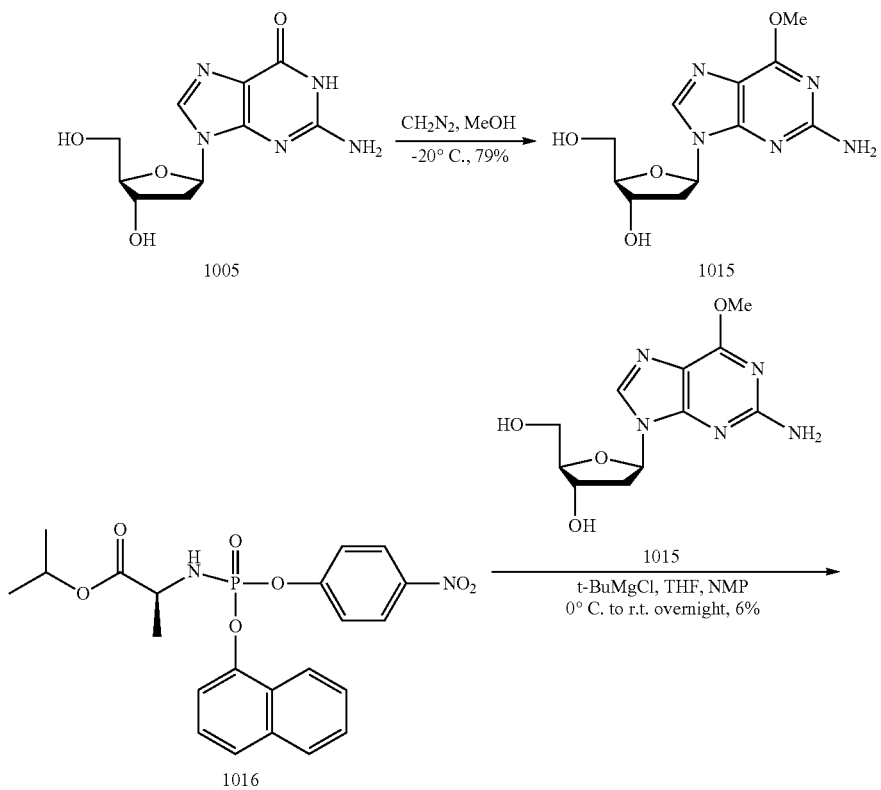

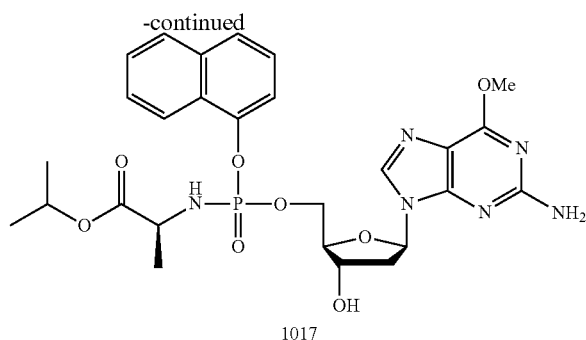

1017

General Procedure for the Preparation of Compound 1017 isopropyl ((((2R,3S,5R)-5-(2-amino-6-methoxy-9H-purin-9-yl)-3-hydroxytetrahydrofuran-2-yl)methoxy)(naphthalen-1-yloxy)phosphoryl)-L-alaninate To a solution of compound 1005 (3.0 g, 11.2 mmol, 1.0 eq) in MeOH (200 mL) at −20° C. was added excess $CH_2N_2$ etherate and stirred for 4 h. The reaction was monitored by LCMS. The resulting mixture was concentrated, triturated with MeOH, and filtered. The filtrate was concentrated to afford crude compound 1015 (2.5 g, 79%) as white powder, which was used for next step without further purification. To a solution of compound 1016 (2.0 g, 4.37 mmol, 1.0 eq) in THF (6 mL) and NMP (25 mL) at 0° C. was added 1.0 M t-BuMgCl (6.55 mL, 6.55 mmol, 1.5 eq). The mixture was stirred at 0° C. for 0.5 h and a solution of compound 1015 (2.5 g, 8.9 mmol, 2.04 eq) in THF (8 mL) was added. The mixture was warmed to room temperature and stirred for 16 h. A saturated aqueous solution of $NH_4Cl$ (25 mL) was added and the organic phase was extracted with ethyl acetate (2×40 mL). The combined organic layer was dried over sodium sulfate, filtered, and concentrated. The crude product was dissolved in MeOH and purified by prep-HPLC to afford compound 1017 (158 mg, 6%, >95% purity) as white solid. LCMS: m/z (ESI+) 601.3 [M+1]$^+$, expected 601.2, $^1$H NMR (400 MHz, DMSO-d6) δ8.09 (t, J=6.4 Hz, 1H), 7.95-7.87 (m, 2H), 7.71 (t, J=7.2 Hz, 1H), 7.56-7.43 (m, 2H), 7.40-7.35 (m, 2H), 6.44 (d, J=2.4 Hz, 2H), 6.23-6.13 (m, 2H), 5.46 (t, J=4.8 Hz, 1H) 4.84-4.73 (m, 1H), 4.42-4.39 (m, 1H), 4.34-4.28 (m, 1H), 4.24-4.18 (m, 1H), 4.12-4.04 (m, 1H), 3.98 (s, 3H), 3.93-3.76 (m, 1H), 2.61-2.47 (m, 1H), 2.25-2.13 (m, 1H), 1.19 (d, J=7.2 Hz, 3H), 1.09-1.03 (m, 6H).

Example 1

Synthetic Protocols (Method C)

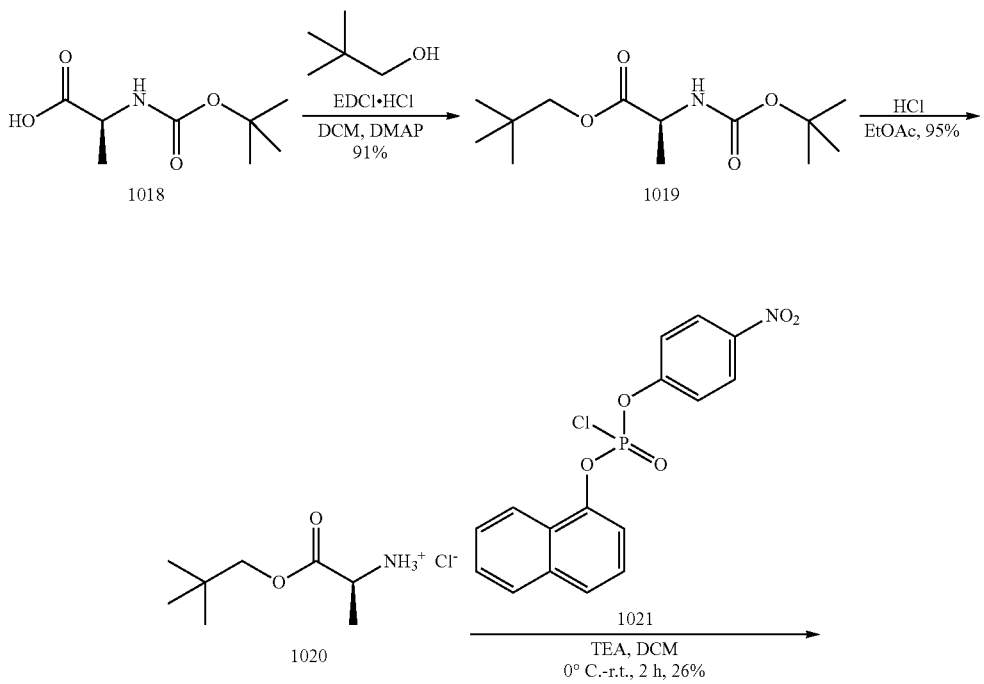

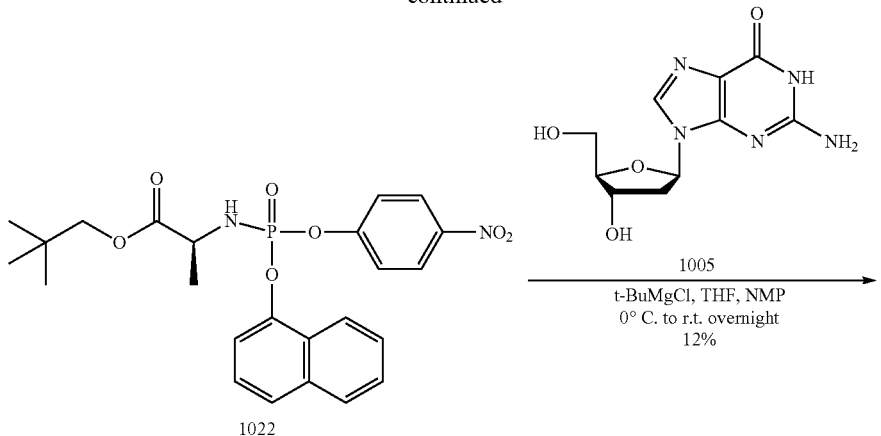

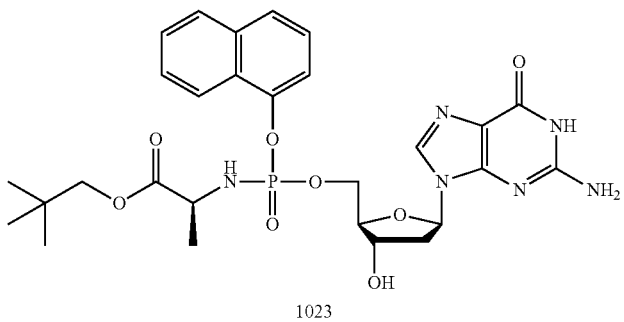

General Procedure for the Preparation of Compound 1023 neopentyl ((((2R,3S,5R)-5-(2-amino-6-oxo-1,6-dihydro-9H-purin-9-yl)-3-hydroxytetrahydrofuran-2-yl)methoxy)(naphthalen-1-yloxy)phosphoryl)-L-alaninate To a mixture of compound 1018 (10 g, 52.8 mmol, 1.0 eq) and neopentyl alcohol (5.58 g, 63.4 mmol, 1.2 eq) in DCM (100 mL) at 0° C. under nitrogen atmosphere was added DMAP (0.64 g, 5.28 mmol, 0.1 eq) and EDCl. HCl (15.2 g, 79.3 mmol, 1.5 eq). The reaction mixture was warmed to rt and stirred for 16 h. The reaction was monitored by TLC. The mixture was extracted with ethyl acetate (3×100 mL). The organic phase was washed with brine, dried over $Na_2SO_4$ and concentrated under reduced pressure. The residue was purified by flash chromatography on silica ($Et_2O$/EtOAc=30:1) to give compound 1019 (12.5 g, 91%) as colorless oil.

To a solution of compound 1019 (6.16 g, 23.8 mmol, 1.0 eq) in HCl/EtOAc solution (2 M, 50 mL, 100 mmol) was stirred at rt for 1 h. The reaction was monitored by $^1$H NMR. The mixture was concentrated under reduced pressure to give compound 1020 (4.42 g, 95%) as white powder.

A mixture of compound 1020 (1.0 g, 5.1 mmol, 1.0 eq), compound 1021 (3.7 g, 10.2 mmol, 2.0 eq) in DCM (10 mL) at 0° C. was added triethylamine (2.23 mL, 16.1 mmol, 3.15 eq). The reaction mixture was warmed to rt and stirred for 2 h. The reaction was monitored by TLC. Then the mixture was extracted with EtOAc (3×20 mL). The organic phase was washed with brine, dried over sodium sulfate and concentrated under reduced pressure. The residue was purified by flash chromatography on silica ($Et_2O$/EtOAc=50:1-30:1-1:1) to give compound 1022 (650 mg, 26%) as a white solid.

To a solution of compound 1022 (660 mg, 1.36 mmol, 1.0 eq) in THF (2.77 mL) and NMP (8.32 mL) at 0° C. was added 1.0 M t-BuMgCl (4.09 mL, 4.08 mmol, 3.0 eq). The mixture was stirred at 0° C. for 0.5 h and a solution of compound 1005 (726 mg, 2.72 mmol, 2.0 eq) in THF (2.77 mL) was added. The mixture was warmed to rt and stirred for 16 h. The reaction was monitored by LCMS. A saturated aqueous solution of $NH_4Cl$ (5 mL) was added and the organic phase was extracted with EtOAc (2×10 mL). The combined organic layers were dried over $Na_2SO_4$, filtered, and concentrated. The crude product was purified by prep-HPLC to afford 1023 (100 mg, 12%, >95% purity) as a white powder. LCMS: m/z (ESI+) 615.4 [M+H]$^+$, expected 615.2, $^1$H NMR (400 MHz, DMSO-d6) δ 10.59 (d, J=2.8 Hz, 1H), 8.10 (t, J=9.6 Hz, 1H), 7.94-7.89 (m, 1H), 7.78-7.56 (m, 2H), 7.54-7.49 (m, 2H), 7.46-7.37 (m, 2H), 6.43 (d, J=4.0 Hz, 2H), 6.23-6.16 (m, 1H), 6.13-6.09 (m, 1H), 5.40 (t, J=4.4 Hz, 1H), 4.38-4.22 (m, 1H), 4.14-4.02 (m, 2H), 3.98-3.87 (m, 2H), 3.74-3.71 (m, 1H), 3.70-3.59 (m, 1H), 2.48-2.33 (m, 1H), 2.21-2.11 (m, 1H), 1.25-1.22 (m, 3H), 0.82 (s, 9H).

Example 1

Synthetic Protocols (Method D)

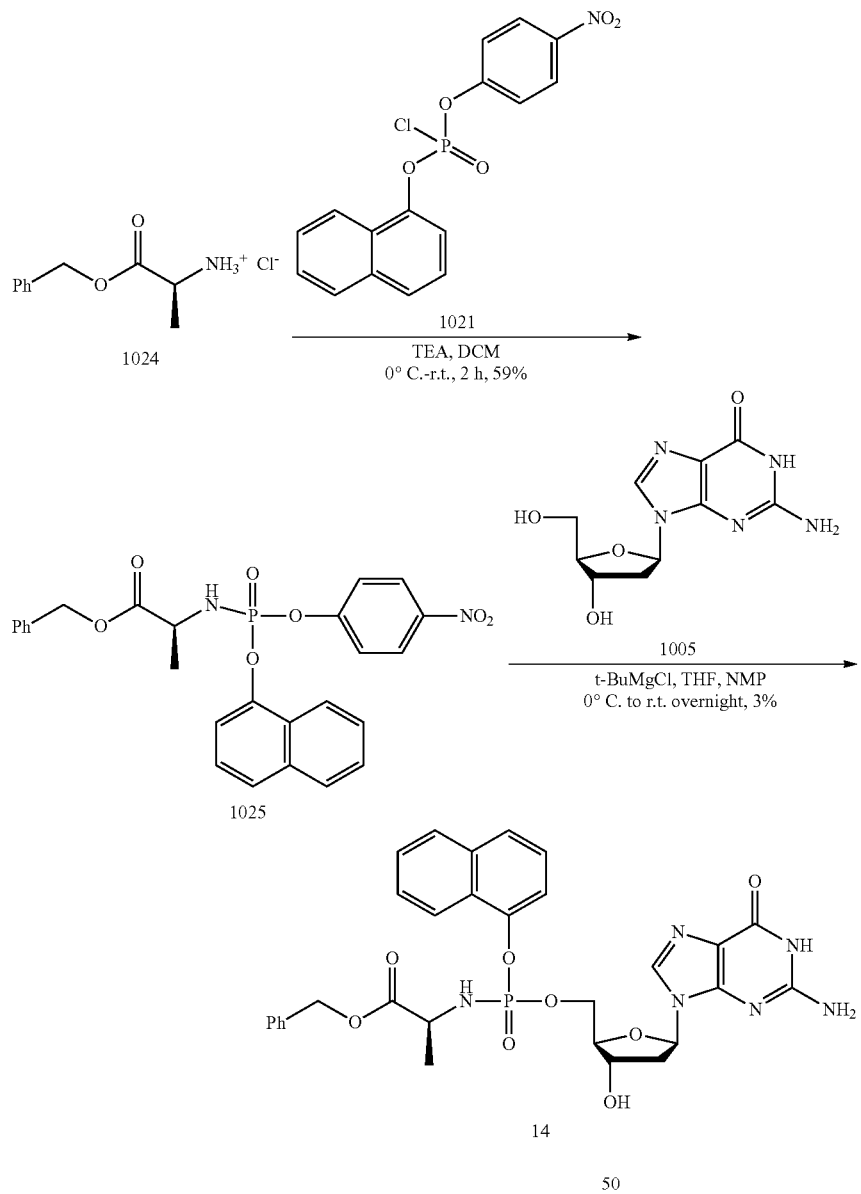

General Procedure for the Preparation of Compound 14 benzyl ((((2R,3S,5R)-5-(2-amino-6-oxo-1,6-dihydro-9H-purin-9-yl)-3-hydroxytetrahydrofuran-2-yl)methoxy)(naphthalen-1-yloxy)phosphoryl)-L-alaninate A solution of compound 1024 (10.0 g, 46.5 mmol, 1.0 eq), compound 1021 (33.8 g, 93 mmol, 2.0 eq) and TEA (13.5 mL, 97.7 mmol, 2.1 eq) in DCM (120 mL) was stirred at 0° C. The mixture was warmed to rt and stirred for 2 h. The reaction was monitored by LCMS. The resulting mixture was quenched with water (250 mL). The organic layer was separated, dried over Na$_2$SO$_4$, filtered, and concentrated under reduced pressure. The crude product was purified by flash chromatography on silica (Et$_2$O/EtOAc=2/1) to give compound 1025 (14 g, 59%) as colorless oil.

To a solution of compound 1025 (5.0 g, 9.88 mmol, 1.0 eq) in THF (15 mL) and NMP (60 mL) at 0° C. was added 1.0 M t-BuMgCl (14.8 mL, 14.8 mmol, 1.5 eq). The mixture was stirred at 0° C. for 0.5 h and a solution of compound 7a (1.98 g, 7.41 mmol, 0.75 eq) in THF (8 mL) was added. The mixture was warmed to rt and stirred for 16 h. A saturated aqueous solution of NH$_4$Cl (60 mL) was added and the organic phase was extracted with ethyl acetate (2×100 mL). The combined organic layer was dried over Na$_2$SO$_4$, filtered, and concentrated. The crude product was purified by prep-HPLC to afford compound 14 (180 mg, 3%, >95% purity) as white solid. LCMS: m/z (ESI+) 635.3 [M+H]$^+$, expected 635.2, NMR (400 MHz, DMSO-d6) δ 10.57 (s, 1H), 8.09 (d, J=7.6 Hz, 1H), 7.92 (d, J=7.2 Hz, 1H), 7.77 (s, 1H), 7.71 (d, J=7.6 Hz, 1H), 7.56-7.48 (m, 2H), 7.45-7.36 (m, 2H), 7.28 (s, 5H), 6.43 (s, 2H), 6.29-6.22 (m, 1H), 6.12

(t, J=6.0 Hz, 1H), 5.40 (d, J=4.0 Hz, 1H), 5.02 (dd, J=12.4, 12.4 Hz, 2H), 4.38-4.32 (m, 1H), 4.26-4.20 (m, 1H), 4.12-4.05 (m, 1H), 4.01-3.93 (m, 2H), 2.48-2.39 (m, 1H), 2.21-2.14 (m, 1H), 1.24-1.20 (m, 6H).

Example 2

Log P (pH 11.0) Assay and Caco-2 Permeability Assay

The Log P assay was performed according to a miniaturized 1-octanol/buffer shake flask method followed by LC/MS/MS analysis. Test compounds were prepared as 10 mM solutions dissolved in 100% DMSO. Test compounds (10 mM in DMSO; 2 µL/well) and QC samples (10 mM in DMSO; 2 µL/well) were transferred in duplicate from storage tubes to the 96-well polypropylene cluster tubes. Buffer was prepared as 80 mM phosphate, 80 mM borate, and 80 mM acetate solution at pH 11.0 with 1% DMSO. Buffer-saturated 1-octanol (149 µL/well) and 1-octanol saturated buffer (149 µL/well) were added to each well. Each of the tubes was vigorously mixed on their sides for 3 minutes and then shaken upright for 1 hour at a speed of 880 rpm at room temperature. The tubes were centrifuged at 2500 rpm for 2 minutes. The buffer layer sample was diluted by a factor of 20 and the 1-octanol layer was diluted by a factor of 200 with internal standard solution. Sample analysis was performed using a triple quadrupole mass spectrometer. Peak areas were corrected by dilution factors and by reference to an internal standard, and the ratio of the corrected peak areas were used to calculate the results (Log P value). Data Analysis—The Log P value for each compound was calculated using the following equation:

$$\text{Log } D_{oct/buffer} = \log\left(\frac{[200 - \text{fold dilution of compound}]_{octanol} \times 200}{[20 - \text{fold compound}]_{buffer} \times 20}\right)$$

The results are presented in Table 3.

The Caco-2 permeability assay was performed as follows. Caco-2 cells purchased from ATCC were seeded onto polyethylene membranes (PET) in 96-well BD Insert plates at $1 \times 10^5$ cells/cm$^2$, and refreshed medium every 4-5 days until to the $21^{st}$ to $28^{th}$ day for confluent cell monolayer formation.

The transport buffer in the study was HBSS with 10 mM HEPES at pH 7.40±0.05. Test compounds were tested at 2 µM in the presence or absence of 30 µM novobiocin (BCRP inhibitor), verapamil (Pgp inhibitor), or GF120918 (BCRP/Pgp inhibitor) bi-directionally in duplicate. E3S control was tested at 5 µM in the presence or absence of efflux inhibitors bi-directionally in duplicate, while fenoterol and propranolol controls were tested at 2 µM in the absence of efflux inhibition in A to B direction in duplicate. Final DMSO concentration was adjusted to less than 1%. The plate was incubated for 120 minutes in a CO$_2$ incubator at 37±1° C., with 5% CO$_2$ at saturated humidity without shaking. All samples were mixed with acetonitrile containing internal standard and centrifuged at 4000 rpm for 20 min. Subsequently, 100 µL supernatant solution was diluted with 100 µLt distilled water for LC/MS/MS analysis. Concentrations of test and control compounds in starting solution, donor solution, and receiver solution were quantified by LC/MS/MS, using peak area ratio of analyte/internal standard, and permeation of lucifer yellow through the monolayer was measured to evaluate the cellular integrity.

The apparent permeability coefficient $P_{app}$ (cm/s) was calculated using the equation:

$$P_{app} = (dC_r/dt) \times V_r/(A \times C_0),$$

where $dC_r/dt$ is the slope of the cumulative concentration of compound in the receiver chamber as a function of time (µM/s); $V_r$ is the solution volume in the receiver chamber (0.075 mL on the apical side, 0.25 mL on the basolateral side); A is the surface area for the transport, i.e. 0.0804 cm$^2$ for the area of the monolayer; and $C_0$ is the initial concentration in the donor chamber (µM). Percent recovery was calculated using the equation:

$$\% \text{ Recovery} = 100 \times [(V_r \times C_r) + (V_d \times C_d)]/(V_d \times C_0),$$

where $V_d$ is the volume in the donor chambers (0.075 mL on the apical side, 0.25 mL on the basolateral side); and $C_d$ and $C_r$ are the final concentrations of transport compound in donor and receiver chambers, respectively. The results are presented in Table 3.

TABLE 3

Log P and Caco-2 data for selected compounds

| Compound | Log P (@ pH = 11) | Caco-2 $P_{app}$ (A – B/B – A × $10^{-6}$)[a] |
|---|---|---|
| dTMP | −1.9 | <0.03/<0.03 |
| 21 | 0.67 | 0.10/7.9 |
| 27 | 0.97 | 0.07/8.9 |
| 24 | 1.7 | 0.04/12.6 |
| dCMP | −2.1 | <0.04/<0.04 |
| 30 | 1.2 | 0.14/0.57 |
| 36 | 1.5 | 0.24/0.66 |
| 33 | 2.1 | 0.19/1.39 |
| dGMP | −1.4 | 0.28/0.51[b] |
| 12 | −0.03 | 0.17/0.64 |
| 18 | 0.24 | 0.16/0.57 |
| 15 | 1.1 | 0.10/1.76 |
| 1017 | 3.0 | 2.0/5.7 |
| 1023 | 1.7 | 0.06/0.49 |
| 14 | 3.4 | 0.04/0.31 |

[a] with efflux inhibitor,
[b] recovery < 2%

Example 3 dNMP Prodrugs Rescue mtDNA Depletion in Patient-Derived Fibroblasts with DGUOK Deficiency Patient-derived fibroblast cell line 10028 containing a DGUOK splicing variant c.592-4_c.592-3delTT and a c.677A>G (p.H226R) resulting in a severe neonatal onset hepatocerebral presentation and mtDNA depletion was used, as described in Buchaklian et. al., *Molecular Genetics and Metabolism*, 2012, 107, 92-94. Cells were cultured in 3.5-cm diameter plates containing αMEM with 10% FBS plus 20 mM L-glutamine. Once confluent, cells were supplemented with serum-starved αMEM plus 20 mM L-glutamine. Compounds were dissolved in DMSO vehicle and added to media containing cells to give a final concentration between 1 and 100 uM. Control cells were supplemented with vehicle only. Cells were incubated with compound or vehicle for 10 consecutive days in serum-starved media, which was exchanged daily with identical media containing freshly prepared compound or vehicle. mtDNA copy number was assessed via qPCR as described in Venegas et. al., *Current Protocols in Human Genetics*, 2011, Chapter 19, Unit 19.7. The results are presented in FIG. 1. Both of the dNMP prodrugs tested, compounds 15 and 1017, were found to increase mtDNA copy number relative to control in a dose-dependent manner.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having the structure of formula (I) or a pharmaceutically acceptable salt thereof:

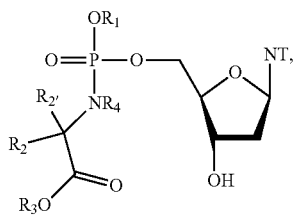

wherein:
$R_1$ is aryl or;
$R_2$ and $R_2'$, each independently, are hydrogen, alkyl, or aralkyl;
$R_3$ is alkyl or aralkyl;
$R_4$ is hydrogen or alkyl;
NT is a nucleobase.

2. The compound of claim 1, wherein the nucleobase is selected from:

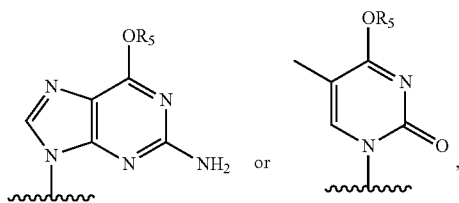

and further wherein $R_5$ is alkyl or aralkyl.

3. The compound of claim 2, wherein $R_5$ is methyl, ethyl, isopropyl, or benzyl.

4. The compound of claim 1, wherein $R_1$ is phenyl, naphthyl, or 4-fluorophenyl.

5. The compound of claim 1, wherein $R_2$ is alkyl.

6. The compound of claim 1, wherein $R_2'$ is H.

7. The compound of claim 1, wherein $R_3$ is methyl, benzyl, neopentyl or isopropyl.

8. The compound of formula (I) in claim 1, wherein the compound is:

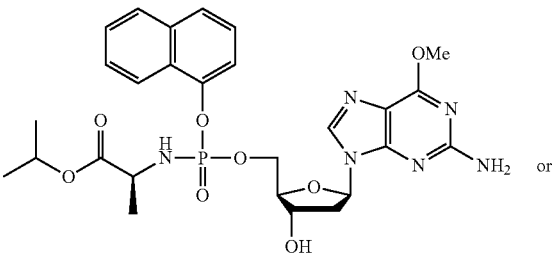

or

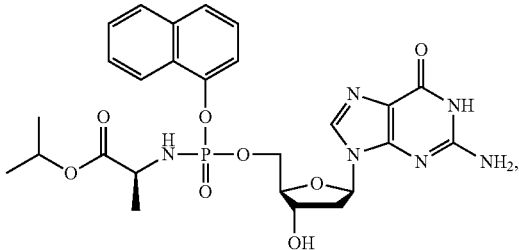

or a pharmaceutically acceptable salt thereof.

9. The compound of claim 1, having the structure of formula (I) or a pharmaceutically acceptable salt thereof:

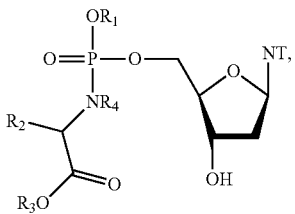

wherein:
$R_1$ is aryl;
$R_2$ is hydrogen, or alkyl or aralkyl;
$R_3$ is alkyl or aralkyl;
$R_4$ is hydrogen or alkyl; and
NT is 9-adeninyl, 9-guaninyl, 1-cytosinyl, or 1-thyminyl.

10. A pharmaceutical composition comprising a compound of claim 1 in combination with a pharmaceutically acceptable carrier.

* * * * *